(12) United States Patent
Maiorino et al.

(10) Patent No.: US 8,403,017 B2
(45) Date of Patent: *Mar. 26, 2013

(54) SYSTEM, METHOD AND APPARATUS FOR MAKING TAPERED LOOPED SUTURE

(75) Inventors: Nicholas Maiorino, Branford, CT (US); Timothy Kosa, Milford, CT (US); William R. Bowns, Ansonia, CT (US)

(73) Assignee: Covidien LP, Mansfield, MA (US)

( * ) Notice: Subject to any disclaimer, the term of this patent is extended or adjusted under 35 U.S.C. 154(b) by 492 days.

This patent is subject to a terminal disclaimer.

(21) Appl. No.: 12/582,982

(22) Filed: Oct. 21, 2009

(65) Prior Publication Data

US 2010/0101707 A1    Apr. 29, 2010

Related U.S. Application Data

(60) Provisional application No. 61/108,581, filed on Oct. 27, 2008.

(51) Int. Cl.
 *B32B 37/00* (2006.01)
(52) U.S. Cl. .............. 156/494; 156/530; 156/580.2
(58) Field of Classification Search .............. 156/73.2, 156/257, 268, 494, 510, 530, 538, 539, 580.1, 156/580.2
See application file for complete search history.

(56) References Cited

U.S. PATENT DOCUMENTS

| | | |
|---|---|---|
| 2,514,184 A | 7/1950 | Lower |
| 3,513,848 A | 5/1970 | Winston et al. |
| 3,657,056 A | 4/1972 | Winston et al. |
| 3,874,963 A | 4/1975 | Barger |
| 4,575,372 A * | 3/1986 | Gundersen ................ 623/1.41 |
| 4,662,068 A | 5/1987 | Polonsky |
| 4,950,285 A | 8/1990 | Wilk |
| 5,226,535 A | 7/1993 | Rosdhy et al. |
| 5,259,846 A | 11/1993 | Granger et al. |
| 5,383,905 A | 1/1995 | Golds et al. |
| 5,403,331 A | 4/1995 | Chesterfield et al. |
| 5,417,700 A | 5/1995 | Egan et al. |
| 5,893,880 A | 4/1999 | Egan et al. |
| 6,077,277 A | 6/2000 | Mollenauer et al. |
| 6,089,438 A | 7/2000 | Suzuki |
| 6,174,324 B1 | 1/2001 | Egan et al. |
| 6,217,591 B1 | 4/2001 | Egan et al. |
| 6,286,746 B1 | 9/2001 | Egan et al. |

(Continued)

FOREIGN PATENT DOCUMENTS

| | | |
|---|---|---|
| EP | 2184157 A1 | 5/2010 |
| FR | 2729940 A | 8/1996 |

(Continued)

OTHER PUBLICATIONS

European Search Report for EP 09252488.3-2310 date of completion is Jan. 11, 2010 (3 pages).

(Continued)

*Primary Examiner* — James Sells
(74) *Attorney, Agent, or Firm* — Covidien LP

(57) ABSTRACT

A system and method for forming a looped suture having a tapered cut is provided. The system includes a base for selectively retaining a portion of thread, a clamping device for receiving a first end of the thread, a tensioning device for receiving a second end of the thread, and a welding/cutting assembly configured to join a first section and second section of the thread to form a loop and to form a tapered end on the first section of the thread. A die for forming a looped suture having a tapered cut is also provided.

10 Claims, 6 Drawing Sheets

U.S. PATENT DOCUMENTS

| | | | |
|---|---|---|---|
| 6,296,659 B1 | 10/2001 | Foerster | |
| 6,358,271 B1 | 3/2002 | Egan et al. | |
| 6,409,743 B1 | 6/2002 | Fenton, Jr. | |
| 6,488,690 B1 | 12/2002 | Morris et al. | |
| 6,669,705 B2 | 12/2003 | Westhaver et al. | |
| 7,090,111 B2 | 8/2006 | Egan et al. | |
| 7,429,266 B2 | 9/2008 | Bonutti et al. | |
| 7,533,791 B2 | 5/2009 | Steiner et al. | |
| 7,582,097 B2 | 9/2009 | McRury et al. | |
| 8,056,599 B2 * | 11/2011 | Maiorino et al. | 156/530 |
| 2004/0122451 A1 | 6/2004 | Wood | |
| 2005/0165448 A1 | 7/2005 | Egan et al. | |
| 2005/0166384 A1 * | 8/2005 | Lenihan et al. | 29/433 |
| 2006/0025858 A1 | 2/2006 | Alameddine | |
| 2006/0259076 A1 | 11/2006 | Burkhart et al. | |
| 2009/0216269 A1 | 8/2009 | Harington et al. | |
| 2009/0248070 A1 | 10/2009 | Kosa et al. | |
| 2009/0259251 A1 | 10/2009 | Cohen | |

FOREIGN PATENT DOCUMENTS

| | | |
|---|---|---|
| JP | 09155979 A | 6/1997 |
| WO | WO 96/25109 A | 8/1996 |
| WO | WO 99/26542 A | 6/1999 |
| WO | WO 02/22025 | 3/2002 |
| WO | WO 02/22025 A | 3/2002 |

OTHER PUBLICATIONS

European Search Report for EP 10 25 0847 mailed Sep. 3, 2010, which application corresponds to U.S. Appl. No. 12/751,456, filed Mar. 31, 2010.

European Search Report for EP 12163417.4-2310 date of completion is May 21, 2012 (10 pages).

European Search Report for EP 12163323.4-2310 date of completion is Jul. 25, 2012 (7 pages).

* cited by examiner

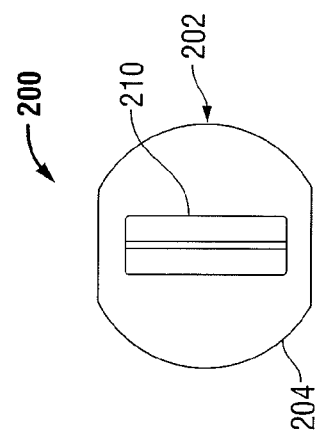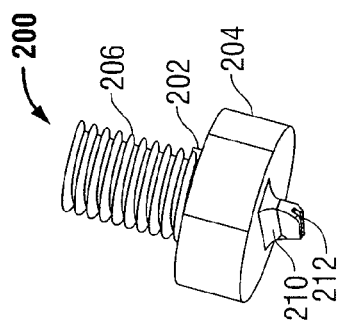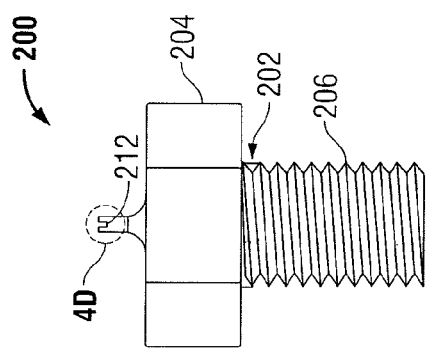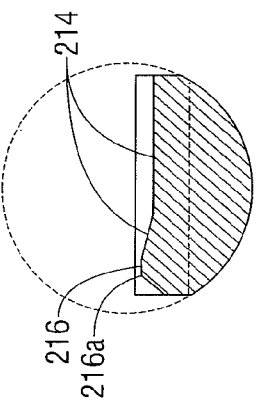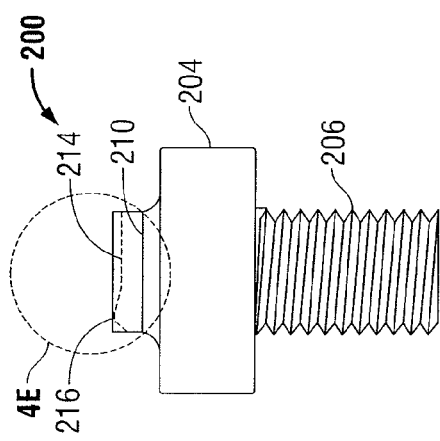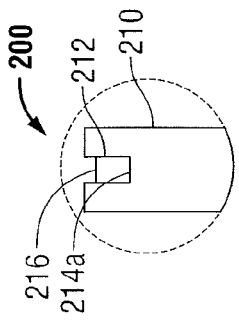

SYSTEM, METHOD AND APPARATUS FOR MAKING TAPERED LOOPED SUTURE

CROSS-REFERENCE TO RELATED APPLICATION

The present application claims benefit to and priority from U.S. Provisional Application No. 61/108,581, filed Oct. 27, 2008, the entire disclosure of which is incorporated by reference herein.

BACKGROUND

1. Technical Field

The present disclosure relates to a method of forming a looped suture. More particularly, the present disclosure relates to a method of forming a looped suture having a tapered cut.

2. Background of Related Art

A method for forming a loop in a suture during a wound closing procedure is known. The method includes using a device to ultrasonically weld together first and second ends of a suture that have been received through opposing sections of tissue. The welding of the suture ends forms a loop that retains the opposing sections of tissue adjacent one another, thereby assisting in the healing of the wound. Because the loop is formed in the suture after the suture has been received through tissue of a patient, to be useful for any practical purpose, the ultrasonic device must be configured for handheld operation. In this manner, a clinician may operate the device in an operating room or a doctor's office. As with all handheld devices, the configuration and effectiveness of the handheld ultrasonic device is limited by its size and weight. The limitations created by the size and weight restrictions of the device become apparent during the forming of a loop on a suture prior to engagement with tissue.

Therefore, it would be beneficial to have a system and method for more effectively forming a loop on a suture prior to engagement of tissue with the suture. It would be further beneficial if the system and method could form a tapered end on the loop.

SUMMARY

Accordingly, a system for forming a looped suture having a tapered cut is provided. The system includes a base for selectively retaining a portion of thread, a clamping device for receiving a first end of the thread, a tensioning device for receiving a second end of the thread, and a welding assembly configured to join a first section and a second section of the thread to form a loop. The welding assembly may further comprises a cutting assembly, which forms a tapered end on the first section of the thread.

The base may include a suture nest, a pin retaining member, a pin, and a pin locking member. The pin retaining member may be pivotally mounted to the base. The pin may be configured to receive a portion of the thread thereabout. The base may include at least one channel for receiving at least a portion of the second section of the thread. The cutting assembly of the system may include a die having a suture engaging portion and a suture cutting portion. In one embodiment, the welding assembly is moved relative to the base. Alternatively, the base is moved relative to the welding assembly. The welding assembly is configured for operable connection to an ultrasonic generator.

A method of forming a loop in a thread is also provided. The method including the steps of providing a loop forming system including, a base for securely retaining a thread to be formed, a clamp for retaining a first end of the thread, a tensioning member for retaining a second end of the thread and applying tension to the thread, and a welding assembly for forming a loop having a tapered end in the thread, securing a portion of the thread to the base such that a first section of the thread is maintained adjacent to a second section of the thread, approximating the welding assembly and the base towards each other, fusing the first section of thread to the second section of thread, cutting a tapered end on a proximal end of the first section of the thread, approximating the welding assembly and base away from each other, and optionally removing the formed suture from the base. The welding assembly may further include a cutting assembly which has a die having a thread engaging portion and a thread cutting portion.

A die for forming a looped suture is also provided. The die includes a base portion, a connecting portion extending from the base portion configured for selectively engaging an ultrasonic device, and a suture mount extending from the base portion opposite the connecting portion. The suture mount includes a thread engaging portion and thread cutting portion configured to form a loop having a tapered end in a thread. The connecting portion may include threads. The thread engaging portion may be flat. The base portion may be configured to be selectively engaged by a removal/installation tool.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 4A is front view of a die for forming a looped suture in accordance with an embodiment of the present disclosure;

FIG. 4B is a side view of the die of FIG. 4A;

FIG. 4C is top view of the die of FIGS. 4A and 4B;

FIG. 4D is an enlarged view of portion 4D of FIG. 4B;

FIG. 4E is an enlarged cross-sectional view of portion 4E of FIG. 4A;

FIG. 4F is a perspective view of the die of FIGS. 4A-4E;

DETAILED DESCRIPTION

Figure 1A:
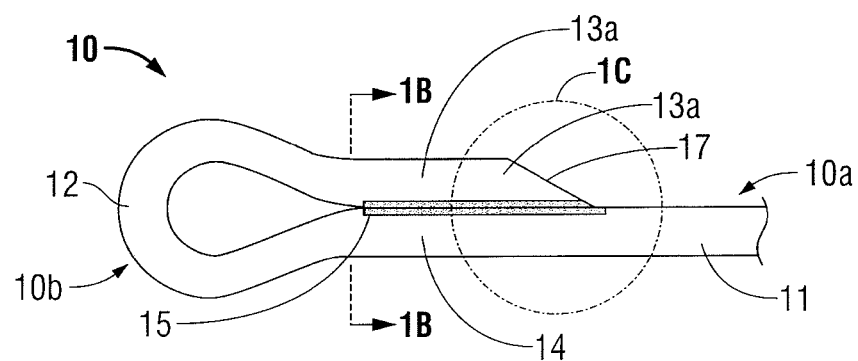
FIG. 1A is a side view of a looped suture including a tapered portion.
Figure 1B:
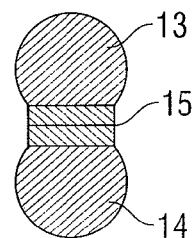
FIG. 1B is a cross-sectional end view of the looped suture of FIG. 1A, taken along line 1B-1B.
Figure 1C:
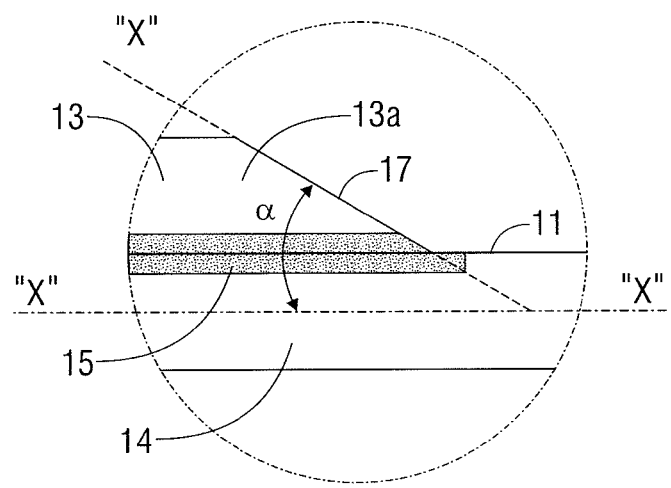
FIG. 1C is an enlarged side view of portion 1C of FIG. 1A.

A method for forming a looped suture including a tapered cut is herein described. Referring initially to FIGS. 1A-1C, a looped suture formed in accordance with a method of the present disclosure is shown generally as looped suture 10. Suture 10 is formed from a monofilament thread 11; however, it is envisioned that suture 10 may be formed from braided threads, multifilament threads and other surgical fibers. Although shown having a circular cross-sectional geometry, the cross-sectional geometry of thread 11 may be of any suitable shape, e.g., round, elliptical, square, flat, octagonal, and rectangular. Thread 11 may be formed of degradable materials, non-degradable materials, and combinations thereof. Thread 11 may be formed using any technique within the purview of those skilled in the art, such as, for example, extrusion, molding and/or gel spinning.

With reference to FIGS. 1A and 1B, looped suture 10 includes a loop 12 formed on a distal end 10b thereof. Loop 12 forms a substantially teardrop shape and may be formed of any size. A first section 13 of monofilament thread 11 overlays a second section 14 of thread 11 to form loop 12. The adjacent surfaces of first and second sections 13, 14 form a joined segment or joint 15. As shown, joined segment 15 extends beyond first section 13 of thread 11. In this manner, first and second sections 13, 14 of thread 11 are less likely to separate or peel away from each other as looped suture 10 is pulled through tissue (not shown).

As will be described in further detail below, first and second sections 13, 14 of thread 11 are welded together to form joined section 15. In this manner, first and second sections 13, 14 of thread 11 are locally heated until each fuses to form joined segment 15. Various types of energy may be used to locally heat first and second sections 13, 14 to form joined segment 15, including, radio frequency (RF), ultrasonic, laser, electrical arc discharge, and thermal. Alternatively, first and second sections 13, 14 of thread 11 may be joined using glue, epoxy or other adhesive.

With particular reference to FIG. 1C, a proximal end 13a of first section 13 is angled to form a tapered surface 17. Tapered surface 17 angles downwardly towards proximal end 10a of looped suture 10. Tapered surface 17 may form an angle between zero degrees)(0°) and ninety degrees (90°), and preferably from about fifteen degrees (15°) to about sixty degrees (60°). Tapered surface 17 facilitates insertion of loop 12 into or through tissue (not shown). In one embodiment, tapered surface 17 is formed such that joined segment 15 extends beyond first section 13 of thread 11. In this manner, tapered surface 17 forms a smooth transition with second section 14 of thread 11, thereby decreasing the likelihood that first and second sections 13, 14 might separate or peel away from each other as looped suture 10 is pulled through tissue.

Although shown having a substantially planar taper, tapered surface 17 may include any number of configurations. For example, tapered surface 17 may be beveled, may include a laterally and longitudinally concave taper, may include a laterally and longitudinally convex taper, or may include any combination thereof. The angle and/or configuration of tapered surface 17 may be selected depending on the tissue being sutured and/or the depth loop 12 is desired to be received within the tissue (not shown).

A system for forming loop 12 on distal end 10b of looped suture 10 will now be described with reference to FIGS. 2A-6C, and is shown generally as system 100. System 100 includes a fixture member or base 110, a suture retaining member 120 (FIG. 3A), a suture tensioning member 125 (FIG. 3A), and a welding/cutting assembly 130 (FIGS. 3A and 3B).

Figure 2A:
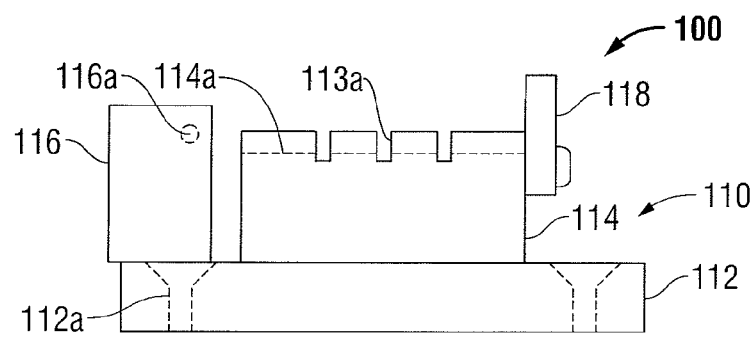
FIG. 2A is a front view of a base for using in the tapered loop forming method of the present disclosure.
Figure 2B:
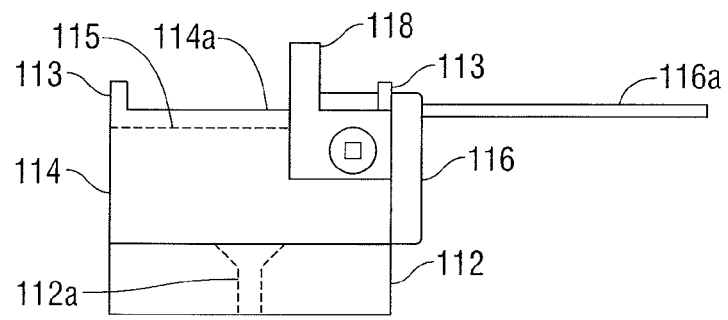
FIG. 2B is a side view of the base of FIG. 2A.
Figure 2C:
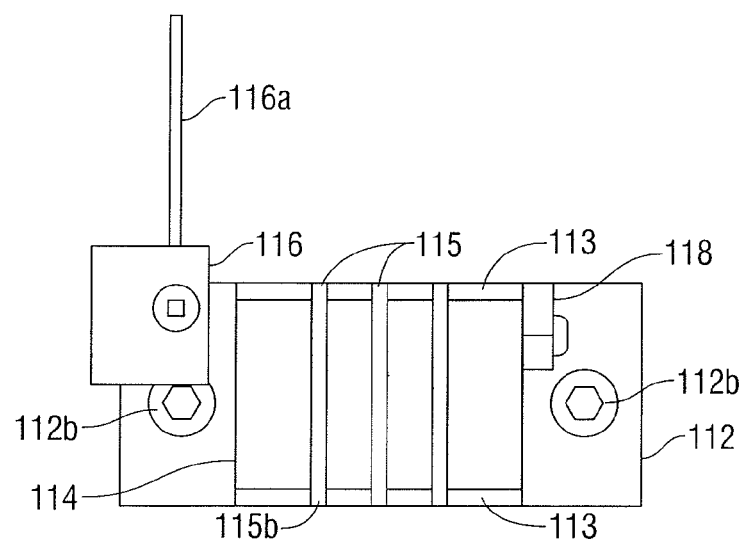
FIG. 2C is a top view of the base of FIGS. 2A and 2B.

Referring initially to FIGS. 2A-2C, base 110 includes a platform 112, a suture nest 114, a pin retaining member 116, a pin 116a extending from pin retaining member 116 and a pin lock 118. Platform 112 includes one or more openings 112a for securing base 110 to a workstation (not shown) using bolts 112b or other suitable fixation means. As shown, suture nest 114 is integrally formed with platform 112. Alternatively, suture nest 114 is releasably attached or securely affixed to platform 112. Nest 114 includes one or more channels 115 extending across a top surface 114a thereof. As will be described in further detail below, channels 115 are configured to partially receive a portion of suture thread 11, including second section 14 (FIG. 1C). Nest 114 further includes raised outer portions 113 extending along proximal and distal ends 115a, 115b of channels 115. In one embodiment, raised outer portions 113 include openings 113a configured to receive two lengths of suture thread 11 adjacent to or on top of one another. As shown, suture nest 114 includes three channels 115; however, it is envisioned that suture nest 115 may include one or more channels 115. In one embodiment, suture nest 114 may be formed without a channel. In this manner, first and second portions 13, 14 of suture thread 11 are received in opening 113a and are maintained adjacent to one another through the tension applied by suture tensioning means 125 (FIG. 3A).

Still referring to FIGS. 2A-2C, pin 116a extends from pin retaining member 116. Pin retaining member 116 is pivotally attached to platform 112 such that pin 116a may be selectively positioned and securely retained perpendicular to channels 115 along an end thereof (FIG. 3B). Pin lock 118 is pivotally attached to suture nest 114 and is configured to secure pin 116a in the perpendicular position adjacent proximal end 115a of channels 115. Alternatively, pin lock 118 is integrally formed with suture nest 114. In another embodiment, pin retaining member 116 is releasably attached or securely affixed to platform 112. The diameter of pin 116a may be varied depending on the desired size of loop 12.

Figure 3A:
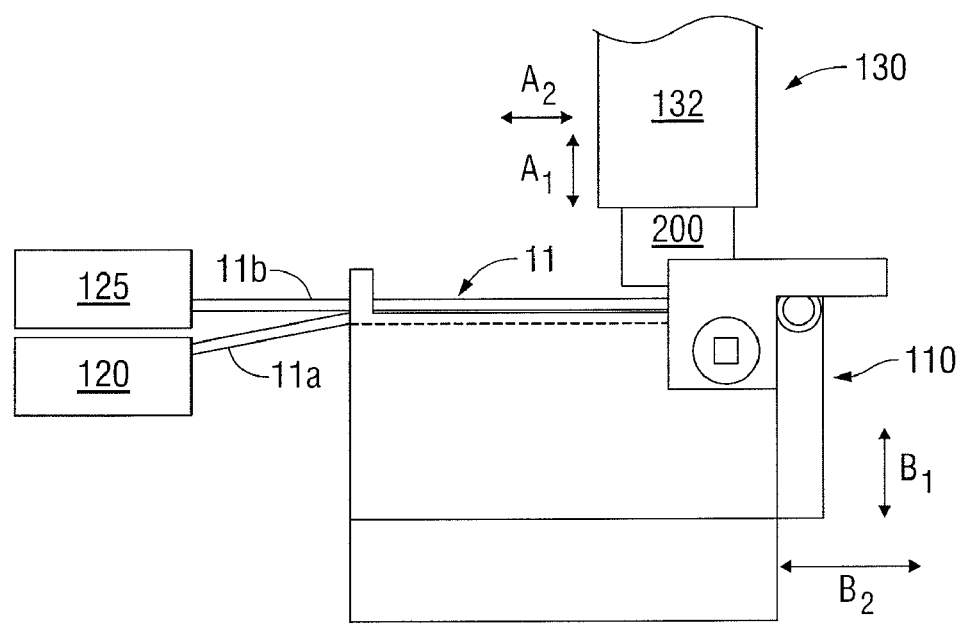
FIG. 3A is a side view of the base of FIGS. 2A-2C loaded with a suture and including a welding assembly, a suture retaining assembly and a suture tensioning assembly.
Figure 3B:
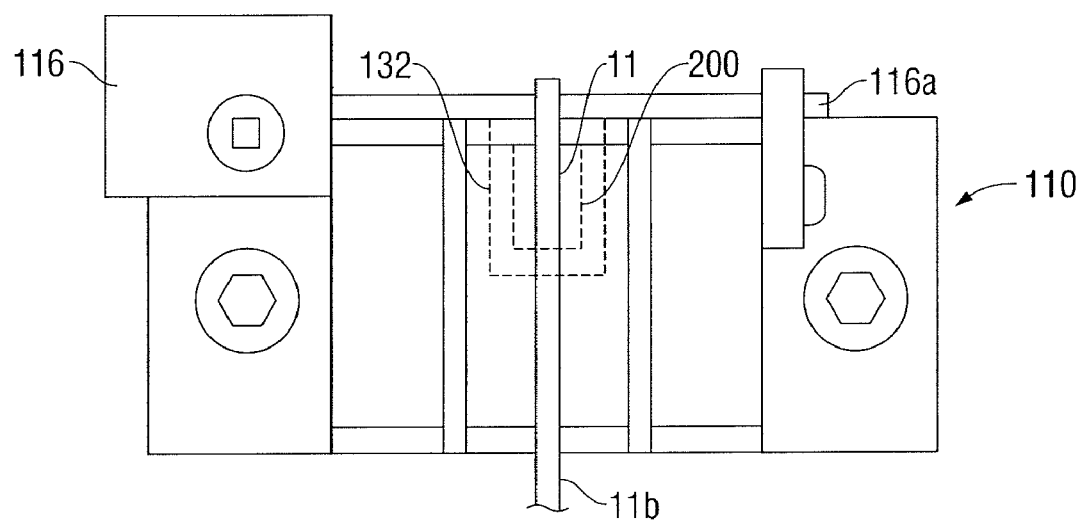
FIG. 3B is a top view of the loaded base of FIG. 3A.

Turning briefly to FIG. 3A, as discussed above, system 100 also includes suture retaining means 120 and suture tensioning means 125. Suture retaining means 120 may include a clamp or other device configured to retain a proximal end 11a of suture thread 11. Suture tensioning means 125 may include a hydraulic or pneumatic tensioning cylinder or other tensioning device configured to receive a distal end 11b of suture thread 11 and to apply tension to suture thread 11 once thread 11 has been securely received about pin 116a. Suture retaining means 120 and suture tensioning means 125 are positioned adjacent distal end 115b of channel 115 to securely receive respective proximal and distal ends 11a, 11b of suture thread 11 during the forming of loop 12.

With reference to FIGS. 3A and 3B, welding/cutting assembly 130 includes an ultrasonic device 132 operably connected to a generator (not shown) for ultrasonically vibrating a die 200 extending from ultrasonic device 132. In one embodiment, welding/cutting assembly 130 is operatively mounted on a press assembly (not shown) for approximating die 200 of welding/cutting assembly 130 towards and away from base 110, in the direction of arrows "$A_1$", to engage and disengage, respectively, thread 11. The press assembly may further be configured to move welding/cutting assembly 130 along thread 11, in the direction of arrows "$A_2$". In an alternative embodiment, welding/cutting assembly 130 is securely mounted relative to base 110 and base 110 is raised and lowered with respect to welding/cutting assembly 130, in the direction of arrows "$B_1$", and is moved laterally with respect to welding/cutting assembly 130, in the direction of arrows "$B_2$". In another embodiment, either or both of base 110 and welding/cutting assembly 130 are moved relative to each other.

With reference now to FIGS. 4A-4F, in one embodiment, die 200 defines a substantially bolt like member 202 including a base 204 and a threaded extension 206. Threaded extension 206 is configured for operable engagement with a press (not shown). Base 204 is configured to be engaged by a removal/installation tool such as a wrench (not shown). In this manner, die 200 may be replaced as necessary. A suture mount 210 extends from base 204 and defines a channel 212 for receiving first section 13 of thread 11 (FIG. 1A). Although shown including channel 212, it is envisioned that base 204 may instead form a substantially flat thread engaging surface.

Still referring to FIGS. 4A-4F, formed within channel 212, suture mount 210 includes a thread engaging portion 214 and a thread cutting portion 216. Thread cutting portion 216 includes a rounded edge 216a having a substantially flat cutting surface for severing the excess portion of first section 13 of thread 11 and forming tapered surface 17. In an alternative embodiment, edge 216a may include a convex, concave and/or beveled cutting surface for forming a concave, convex and/or beveled tapered surface 17. Thread engaging portion 214 of suture mount 210 defines a substantially planar surface 214a. In alternative embodiments, thread engaging portion 214 of suture mount 210 may define a surface corresponding to the contour of suture thread 11. In this manner, thread engaging portion 214 may include a concave, convex or beveled surface to correspond with a suture thread having a convex, concave or beveled profile. It is further envisioned that thread engaging portion 214 may include one or more notches (not shown) configured to accommodate barbs (not shown) formed on thread 11. In this manner, the barbs would be received within the notches formed in thread engaging portion 214 and not be flattened during the welding/cutting process. In certain embodiments (not shown), the die does not include a cutting surface, and the cutting step may be performed utilizing a separate cutting blade.

The method of forming looped suture 10 utilizing system 100 will now be described with reference to FIGS. 3A and 5-6C. Referring initially to FIG. 3A, a proximal end 11a of thread 11 is securely locked in a clamp 120. Second section 14 of thread 11 is then positioned within a channel 115 of nest 114. Thread 11 is next wrapped around pin 116a before first section 13 of thread 11 is placed on top of or adjacent second section 14. A distal end 11b of thread 11 is then received in tension cylinder 125. Tensioning cylinder 125 is then activated to tension thread 11 within base 110. To prevent stretching of thread 11 during the forming of looped suture 10, and to thereby maintain the consistency and integrity of thread 11, thread 11 may be formed of a pre-stretched material.

Figure 5:
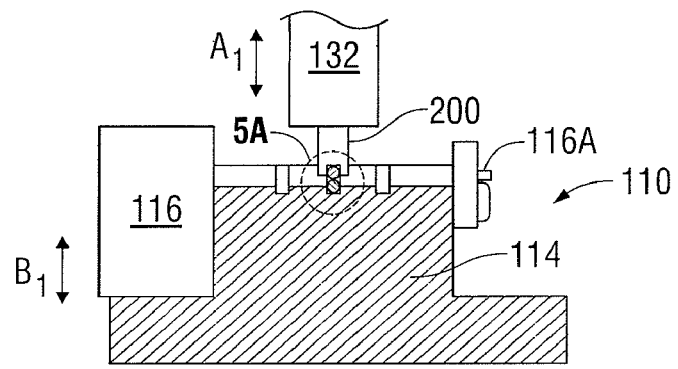
FIG. 5 is a cross-section view of the loaded base of FIGS. 3A and 3B.
Figure 5A:
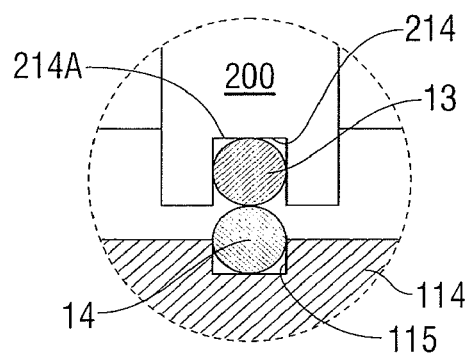
FIGS. 5A and 5B are enlarged views of portion 4 of FIG. 3C, with the suture in pre-welded (FIG. 5A) and post-welded (FIG. 5B) configurations.
Figure 5B:
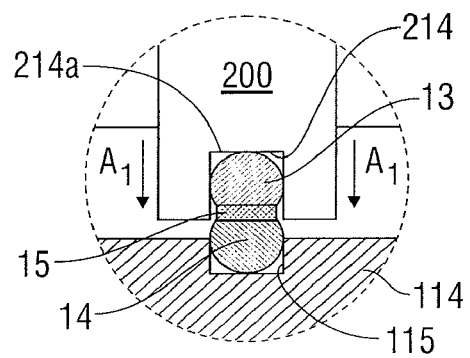
Figure 6A:
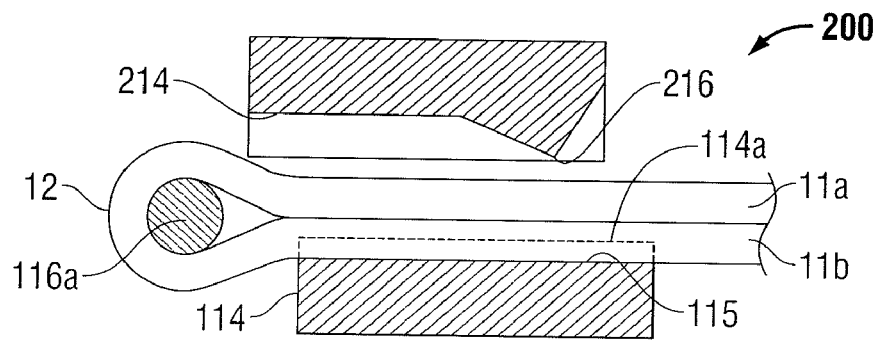
FIG. 6A is an enlarged partial cross-sectional side view of a looped suture forming assembly according to an embodiment of the present disclosure, prior to forming of the loop.
Figure 6B:
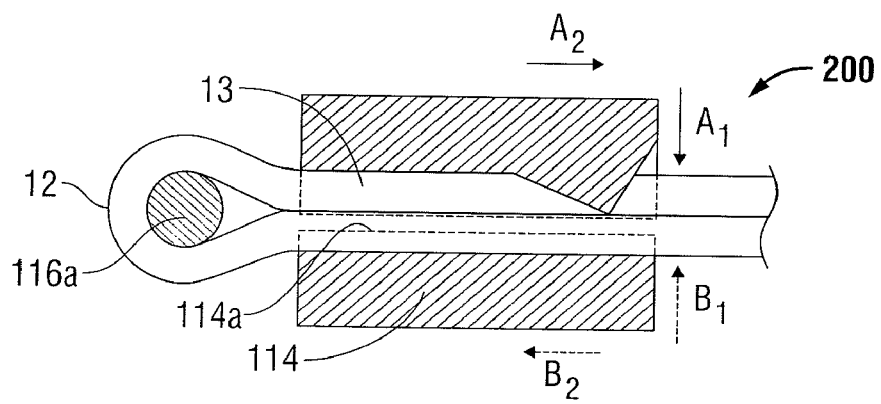
FIG. 6B is an enlarged partial cross-sectional side view of the suture forming assembly of FIG. 6B, during forming of the loop.
Figure 6C:
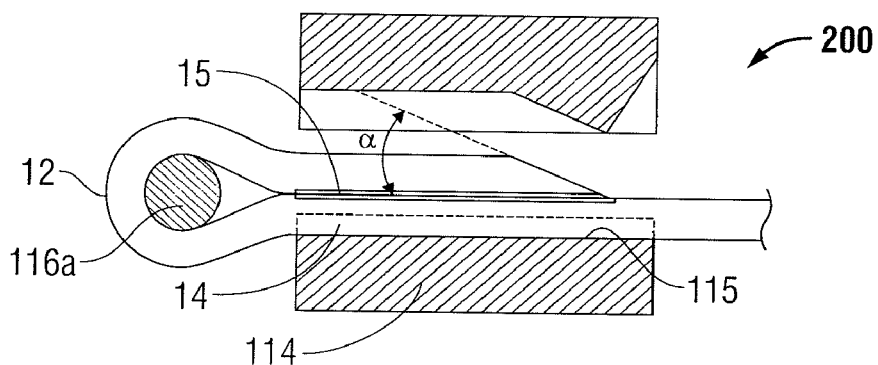
FIG. 6C is an enlarged partial cross-sectional side view of the suture forming assembly of FIGS. 6A and 6B, following formation of the loop.

With particular reference now to FIGS. 5-6C, once first and second sections 13, 14 are positioned adjacent one another, welding/cutting assembly 130 is approximated towards suture nest 114, in the direction of arrow "$A_1$", and laterally with respect to suture nest 114, in the direction of arrow "$A_2$". Alternatively, as discussed above, suture nest 114 may be moved relative to welding/cutting assembly 130, in the direction of arrows "$B_1$", "$B_2$". As welding/cutting assembly 130 and suture nest 114 are approximated, first section 13 of suture thread 11 is received within channel 212 of die 200. Ultrasonic device 132 may be activated at any point during this process to ultrasonically vibrate die 200.

Continued approximation of die 200 toward suture nest 114 causes thread cutting portion 216 of suture mount 110 to engage first section 13. The ultrasonic vibration of die 200 permits thread cutting portion 216 to easily cut through first section 13 as welding/cutting assembly 130 is moved towards suture nest 114. The continued movement of die 200 causes thread engaging portion 214 to engage first section 13 of thread 11. The downward pressure exerted on first section 13 of thread 11 from the continued approximation of die 200 towards nest 114 (FIG. 6B), in combination with ultrasonic vibration of die 200, causes the contacting portions of first and second sections 13, 14 to heat and begin to melt. The melting of the contacting portions of first and second sections 13, 14 causes first and second sections 13, 14 to fuse, thereby creating joined section 15. As thread contacting portion 214 engages first section 13 of thread 11 to form joined section 15, thread cutting portion 216 completely severs distal end 11b of thread 11 from the remainder of thread 11, thereby forming tapered surface 17. In an alternate embodiment, thread cutting portion 216 only partially severs distal end 11b of thread 11 from the remainder of thread 11, thereby requiring subsequent removal of the remainder thread.

The rate at which base 110 and/or welding/cutting assembly 130 are approximated towards one another relative to the rate at which base 110 and/or welding/cutting assembly 130 are laterally moved relative to one another effects angle α (FIG. 6C) of tapered surface 17. The slower base 110 and/or welding/cutting assembly 130 moves laterally relative to the other with respect to the rate of respective, upward and/or downward movement of base 110 and/or welding/cutting assembly 130, the greater is angle α of tapered surface 17. The converse is also true. The rate of lateral movement of base 110 and/or welding/cutting assembly 130 relative to the rate of respective, relative upward and/or downward movement, may be increased to lessen the angle α of tapered surface 17.

Once first and second sections 13, 14 are fused to create joined section 15, welding/cutting assembly 130 is approximated away from suture nest 114 and looped suture 10 is removed from pin 116a. Suture 10 may include flash or debris (not shown) formed during the welding/cutting process. The flash may need to be removed before looped suture 10 may be used.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that loop forming system 100 may include more than one welding/cutting assembly 130 to produce more than one looped suture 10 per activation.

What is claimed is:
1. A system for forming a looped suture having a tapered cut, the system comprising:
   a base for selectively retaining a portion of thread, wherein the base includes a suture nest, a pin retaining member, a pin, and a pin locking member;
   a clamping device for receiving a first end of the thread;
   a tensioning device for receiving a second end of the thread; and a welding assembly configured to simultaneously join a first section and a second section of the thread to form a loop and cut a tapered end in the second section of the thread.

2. The system of claim 1, wherein the pin retaining member is pivotally mounted to the base.

3. The system of claim 1, wherein the pin is configured to receive a portion of the thread thereabout.

4. The system of claim 1, wherein the base includes at least one channel for receiving at least a portion of the second section of the thread.

5. The system of claim 1, wherein the welding assembly includes a die having a suture engaging portion and a suture cutting portion.

6. The system of claim 1, wherein the welding assembly is moved relative to the base.

7. The system of claim 1, wherein the base is moved relative to the welding/cutting assembly.

8. The system of claim 1, wherein the welding assembly is operably connected to an ultrasonic generator.

9. The system of claim 1, wherein the base is configured to retain the thread in a fixed position relative to the base throughout the joining of the first and second sections of the thread and the cutting of the tapered end.

10. The system of claim 1, wherein the welding assembly includes a die configured for forming the loop and cutting a tapered end in the loop.

* * * * *